(12) United States Patent
Irion et al.

(10) Patent No.: US 7,896,526 B2
(45) Date of Patent: Mar. 1, 2011

(54) LIGHT SOURCE FOR ENDOSCOPY OR MICROSCOPY

(75) Inventors: Klaus-Martin Irion, Emmingen-Liptingen (DE); Markus Simmen, Schwarzenbach (CH); Andre Ehrhardt, Wurmlingen (DE); Juerg Steiner, Winterthur (CH)

(73) Assignee: Karl Storz GmbH & Co. KG (DE)

( * ) Notice: Subject to any disclaimer, the term of this patent is extended or adjusted under 35 U.S.C. 154(b) by 496 days.

(21) Appl. No.: 11/442,579

(22) Filed: May 26, 2006

(65) Prior Publication Data

US 2006/0268552 A1    Nov. 30, 2006

(30) Foreign Application Priority Data

May 31, 2005    (DE) .................. 10 2005 026 662

(51) Int. Cl.
   *F25D 3/10*    (2006.01)
(52) U.S. Cl. .................. 362/294; 362/253; 362/261; 362/262; 362/373
(58) Field of Classification Search ............. 362/294, 362/373, 572, 261, 262, 253
   See application file for complete search history.

(56) References Cited

U.S. PATENT DOCUMENTS

| | | | | |
|---|---|---|---|---|
| 5,309,457 A | | 5/1994 | Minch ..................... | 372/34 |
| 5,351,251 A | | 9/1994 | Hodgson .................. | 372/4 |
| 5,560,362 A | | 10/1996 | Sliwa, Jr. et al. ........ | 128/660.03 |
| 6,784,601 B2 | | 8/2004 | Kai et al. ................. | 313/46 |
| 6,880,954 B2 | * | 4/2005 | Ollett et al. .............. | 362/245 |
| 2003/0214803 A1 | * | 11/2003 | Ono et al. ................ | 362/1 |
| 2004/0040327 A1 | * | 3/2004 | Iida et al. ................. | 62/259.2 |
| 2004/0120162 A1 | * | 6/2004 | Tsimerman et al. ...... | 362/573 |
| 2005/0003322 A1 | * | 1/2005 | Logan et al. ............. | 433/29 |
| 2005/0103481 A1 | * | 5/2005 | Kawasaki et al. ........ | 165/133 |
| 2005/0152146 A1 | * | 7/2005 | Owen et al. .............. | 362/294 |
| 2005/0190567 A1 | * | 9/2005 | Childers et al. .......... | 362/373 |
| 2005/0237747 A1 | * | 10/2005 | Shimizu et al. .......... | 362/294 |
| 2006/0002142 A1 | * | 1/2006 | Jeong et al. .............. | 362/612 |
| 2006/0098439 A1 | * | 5/2006 | Chen ........................ | 362/294 |
| 2006/0173245 A1 | * | 8/2006 | Todd et al. ............... | 600/178 |

FOREIGN PATENT DOCUMENTS

| | | |
|---|---|---|
| DE | 25 01 863 | 7/1976 |
| DE | 43 13 583 A1 | 5/1994 |
| DE | 44 10 128 A1 | 10/1994 |
| DE | 101 37 748 A1 | 2/2003 |

(Continued)

OTHER PUBLICATIONS

XBO Catalog, Xenon-Kurzbogenlampen, p. 10.13, 1 page.

(Continued)

*Primary Examiner*—Sandra L O Shea
*Assistant Examiner*—Mary Zettl
(74) *Attorney, Agent, or Firm*—St. Onge Steward Johnston & Reens LLC

(57) ABSTRACT

A light source for endoscopy or microscopy comprises a lamp, a heat sink, the heat sink being thermally connected to the lamp and at least one heat pipe, which is thermally connected to the heat sink and which dissipates the heat that is generated by the lamp and transferred to the heat sink.

15 Claims, 4 Drawing Sheets

FOREIGN PATENT DOCUMENTS

| | | |
|---|---|---|
| JP | 200375081 A * | 3/2003 |
| WO | WO 99/16136 | 4/1999 |
| WO | WO 02/11640 | 2/2002 |
| WO | WO 03/002909 | 1/2003 |
| WO | WO 03/081127 A2 | 3/2003 |
| WO | WO 2004/011848 | 2/2004 |

OTHER PUBLICATIONS

PerkinElmer Optoelectronics, Cermax Xenon Arc Lamps, PE300BF and PE 300BUV, ww.perkinelmer.com/opt, 2 pages.

European Search Report & Written Opinion, Oct. 12, 2006, 5 pages.

* cited by examiner

LIGHT SOURCE FOR ENDOSCOPY OR MICROSCOPY

FIELD OF THE INVENTION

The present invention relates to a light source for endoscopy or microscopy, comprising a lamp and a heat sink, the heat sink being thermally connected to the lamp.

BACKGROUND OF THE INVENTION

Light sources for endoscopy or microscopy are known, and are marketed, e.g. by the applicant, under the name "D-Light System".

Such light sources are used to illuminate an area that is to be inspected with an endoscope, for example. Since the area to be inspected is normally in complete darkness and since the light is usually supplied via light guides, which have only a small cross-section, the light source must provide light of high power or power density in order to ensure adequate illumination within the body. Arc lamps and, more particularly, so-called high-pressure xenon short arc lamps are generally used for this purpose.

In addition to producing a high output of light, such lamps generate a high output of heat. A present-day xenon short arc lamp with a total electrical power rating of 300 W emits less than 50 W as light and more than 250 W as heat. This heat must be drawn away from the lamp and out of the light source, as otherwise it may lead to overheating and damage to the light source.

Light sources of this kind have hitherto been cooled by transferring the heat generated by the lamp to a heat sink that has as large a surface area as possible. By means of fans located in the light source, air is guided through a housing of the light source and over the heat sink and thus carries the heat away from the housing of the light source. This is also referred to as active cooling.

Using fans in the field of medical applications is problematic, however, as such fans can produce layers of dust and dirt in the light sources, e.g. through abrasive wear or the leakage of lubricants. These layers of dust and dirt, particularly in a relatively warm environment of the kind found in the interior of a light source, are a breeding ground for potentially pathogenic bacteria. These bacteria are then in turn carried through the housing by the current of air and into an originally sterile area, where they lead to hygiene problems. The inside of the instrument is not normally cleaned on a regular basis, other than in the context of repairs.

Another problem is that known light sources use fast-rotating, and often non-sound-insulated, fans, which give rise to considerable, often monotonous, noise. Such noise is extremely disturbing to both the surgeon and the patient.

SUMMARY OF THE INVENTION

It is therefore an object of the invention to describe a light source that is cooled without an active current of air from the inside of the instrument into the environment, which can lead to contamination of a sterile area.

In accordance with an aspect of the invention a light source for endoscopy or microscopy is provided, comprising a lamp having a radiating surface, a heat sink being thermally connected to said lamp and at least one heat pipe which is thermally connected to the heat sink and which dissipates the heat that is generated by the lamp and transferred to the heat sink.

A heat pipe is a device consisting of a closed hollow body which is generally made of a thermally highly conductive material, e.g. copper or aluminium. On the internal surface of the hollow body there is a wick-like material that acts as a capillary. The hollow body is in addition filled with a liquid under intrinsic or, if necessary, reduced pressure. If heat is then applied at any site on the surface of the heat pipe, the liquid inside the heat pipe starts to boil and, absorbing heat energy, turns into vapour. This vapour is then distributed in the hollow body and condenses, releasing heat, at a colder part of the heat pipe. The wick-like material that acts as a capillary absorbs the condensed material in turn and transports it back to that part of the heat-pipe where heat is applied. This results in a cycle, by which heat is transported from one part of the heat-pipe to another part in a highly effective manner. Heat pipes can have a thermal conductivity that exceeds that of copper by several orders of magnitude. Heat pipes also have the advantage of being entirely self-contained systems which can transport heat without external influence, e.g. the use of the fans or pumps.

Thus, through the use of at least one heat pipe, heat from a lamp of a light source for endoscopy or microscopy can be effectively drawn away to another place, e.g. to the outside of a housing, without the need to use fans. The housing can be designed as a completely sealed unit, such that no contamination can escape from within it.

The term "heat sink" as used in the context of the invention means any body that can absorb or dissipate heat from the lamp. The body can be of any form and can be made of any material, provided that the latter can absorb the heat from the lamp and convey it to the heat pipe. Metals that are very good conductors of heat, such as copper or copper alloys, are examples of materials for the heat sink.

The term "lamp" as used in the context of the invention includes all lamp types familiar to a person skilled in the art. Arc lamps and, in particular, xenon short arc lamps are preferred lamp types.

The expression "thermally connected" as used in the context of the invention includes any kind of connection that allows the transfer of heat. This includes both direct thermal contact and indirect thermal contact via additional elements.

In one embodiment of the invention there is an electrically highly insulating layer between the lamp and the heat sink.

Because of the high thermal conductivity that is required, the heat sink usually consists of a metal, i.e. a material that conducts electricity. To light a lamp, often very high voltages have to be applied. The striking voltage for a xenon short arc lamp, for example, can be in the 20-30 kV range. With the use of such high voltages to light the lamp, it can happen that the voltage or charge discharges onto the heat sink, which can then transmit the current to the housing or other components. This can endanger a user of the light source or instruments in the vicinity. Through the provision of an electrically insulating layer between the lamp and the heat sink, discharges of this kind can be prevented.

In one embodiment of the abovementioned measure, the electrically insulating layer is thermally conductive.

This measure ensures that the dissipation of the heat from the lamp to the heat pipe is not hindered by the electrically conductive layer.

In one embodiment of the abovementioned measure, the electrically insulating layer is designed so as to reduce structure-borne sound.

The light sources described earlier are also used in so-called pulsed mode, which means that the lamp is switched on and off at short intervals. When the lamp is lighted, noise is produced, and in pulsed mode this can lead to intermittent noise of considerable intensity. The abovementioned measure leads to a reduction of such noise.

In a further embodiment of the invention the electrically insulating layer consists of a nitride ceramic, in particular an aluminium nitride ceramic.

The advantage of nitride ceramics and, in particular, aluminium nitride ceramics is that they have high thermal conductivity and, in addition, are highly resistant to electrical discharges. As a result, these materials provide both good thermal conduction and outstanding electrical insulation.

In a further embodiment of the measure mentioned earlier, the electrically insulating layer comprises a layer of copper on at least one surface; in particular, it comprises a layer of copper on all surfaces.

This measure further optimizes heat transfer at the surface of the electrically insulating layer.

In a further embodiment of the invention, the at least one heat pipe is thermally connected to a heat-accumulating or heat-releasing element at a site some way removed from the heat sink.

The abovementioned measure increases the efficiency of heat dissipation at the heat-pipe site to which the heat carried away by the heat sink is to be conveyed.

In one embodiment of the measure mentioned earlier, the heat-accumulating or heat-releasing element can be thermally connected to several heat pipes. In particular, the several heat pipes belong to different devices.

This measure creates a so-called heat sink bus, whereby different components and, if necessary, even different devices can be cooled with a single heat-accumulating or heat-releasing element.

In a further embodiment of the abovementioned measure the heat-releasing element comprises microstructuring.

This measure increases the surface area of the heat-releasing element. This in turn makes the release of heat into the environment more efficient.

In a further embodiment of the invention the at least one heat pipe can be thermally connected to a support for the light source.

By means of this measure, a support for the light source can also be used for heat dissipation.

In a further embodiment of the invention there is at least one (internal) fan, which generates a current of air across a radiating surface of the lamp.

Heat dissipation at the sides of the lamp that are in contact with the heat sink is generally very efficient. The radiating surface cannot be connected to the heat sink, however, as it must necessarily be open to allow the beam of light to escape. Intense heat which is not efficiently carried away can thus develop there. By means of the abovementioned measure, a build-up of heat at the radiating surface can be prevented.

In a further embodiment of the abovementioned measure the heat sink comprises a flank which projects beyond the radiating surface of the lamp and which is sited downstream of the radiating surface of the lamp in the current of air that can be generated by the fan.

By means of this measure, the air heated by the lamp is directed, by the fan, onto a part of the heat sink, which absorbs at least part of the heat that has been absorbed by this air.

In a further embodiment of the measure mentioned earlier, the flank comprises structures that air can pass through.

By means of this measure, the effective surface area exposed to air heated by the lamp flowing through the heat sink can be greatly increased, making heat transfer more efficient.

In a further embodiment of the measure mentioned earlier, the structures that air can pass through run at least part way along the at least one heat pipe.

By means of this measure, the air heated by the lamp can be guided through the heat sink along a heat pipe, which again makes heat dissipation more efficient.

In a further embodiment of the invention there is also a power supply to supply the lamp with power, the power supply comprising at least one heat pipe to dissipate the heat that is generated.

By means of this measure, it is possible to create a completely enclosed device which comprises all the necessary components, each component being passively cooled, such that no current of air into or out of a housing of the light source is necessary.

It goes without saying that the features mentioned above and those still to be mentioned below can be used not only in the stated combinations but also in other combinations or on their own without leaving the scope of the invention.

BRIEF DESCRIPTION OF THE DRAWINGS

Exemplary embodiments of the invention are presented in the drawings and are explained in greater detail in the description below.

DETAILED DESCRIPTION OF THE INVENTION

Figure 1:
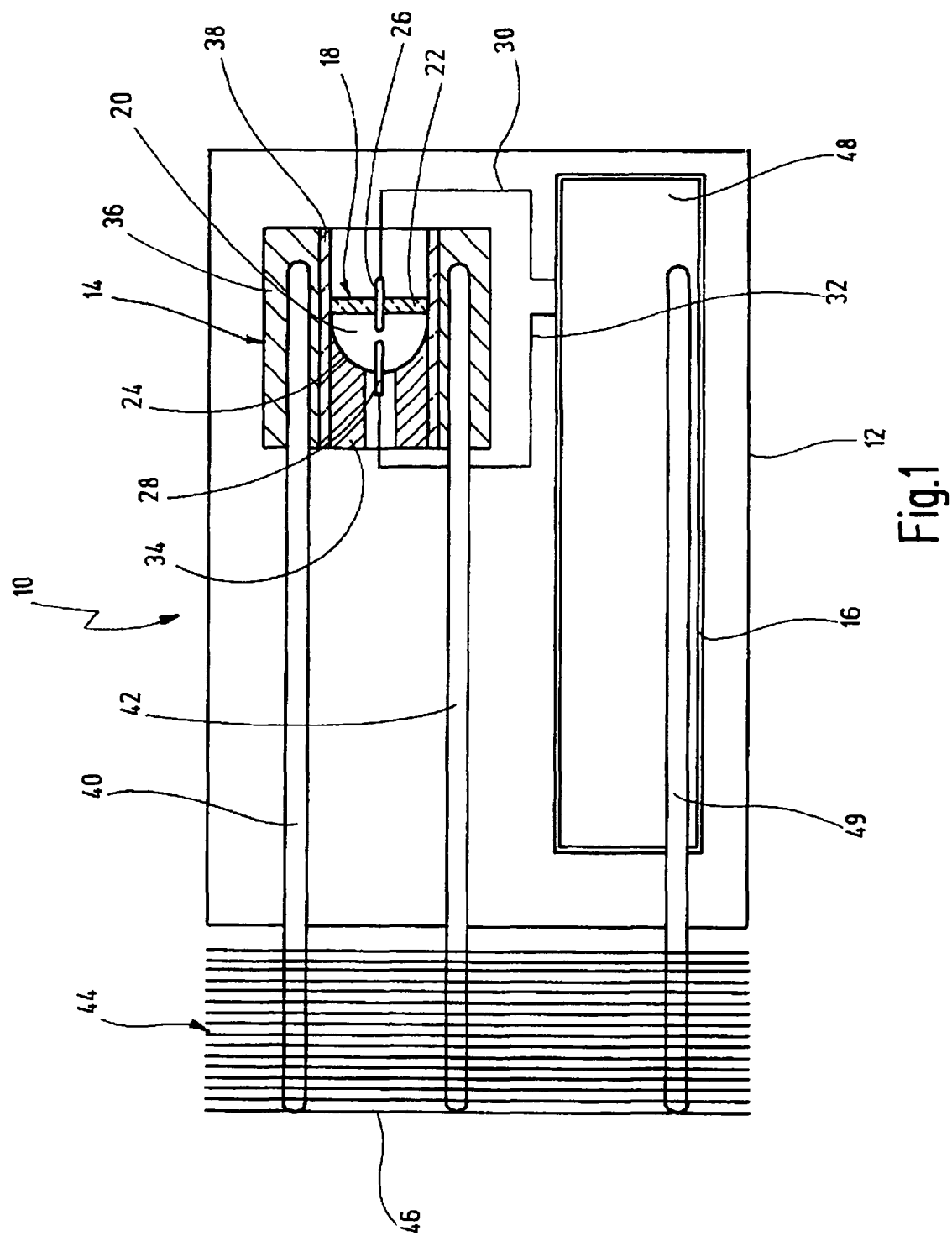
FIG. 1 shows a light source for endoscopy or microscopy.

FIG. 1 shows a light source which as a whole designated by the reference number 10.

The light source 10 comprises a housing 12, in which there is a lamp module 14 and a power supply 16.

The lamp module 14 comprises a lamp, in particular an arc lamp, in particular in the form of a xenon short arc lamp 18. This xenon short arc lamp 18 comprises a xenon-filled interior space 20, which at its front is bordered by a glass plate 22 and on a back surface is bordered by a reflector 24. On opposite sides in the interior space 20 of the lamp there are electrodes 26 and 28, which are connected to the power supply 16 by leads 30 and 32.

If a sufficiently high voltage is applied to the two electrodes 26 and 28 by means of the power supply 16, a continuous electric arc is produced between the electrodes 26 and 28, generating light with a spectrum similar to that of daylight. The voltage needed to produce an electric arc is generally referred to as the striking voltage.

The xenon short arc lamp 18 is in a holder 34, which is located within a heat sink 36. The heat sink 36 here consists of copper and serves to dissipate, as efficiently as possible, the heat generated by the xenon short arc lamp 18.

Between the heat sink 36 and the holder 34 or xenon short arc lamp 18 there is also an electrically insulating layer 38, which here consists of an aluminium nitride ceramic. The surfaces of the electrically insulating layer 38 that are in contact with the heat sink 36 and the holder 34 or the xenon short arc lamp 18 are provided, by means of a technique called Direct Copper Bonding (DCB), with a layer of copper, greatly increasing heat transfer at the surfaces.

In this technique, copper foils comprising copper(I) oxide are placed on the ceramic surfaces that are to be coated. This assembly is then heated until a eutectic forms from the ceramic and the copper(I) oxide, creating, after cooling, a solid bond between the ceramic, the copper(I) oxide, and the copper.

The electrically insulating layer 38 prevents a discharge of voltage from the xenon short arc lamp 18 to the heat sink 36. Since the copper coating is on the surface only, it does not impair the electrical insulation.

There are also heat pipes 40 and 42 connected to the heat sink 36. In this case, the heat pipes 40 and 42 are inserted in holes bored in the heat sink 36; in addition, a thermally conductive paste is introduced between the heat pipes 40, 42 and the heat sink 36 in order to further optimize heat conduction.

Outside the housing 12 of the light source 10 the heat pipes 40, 42 are connected to a heat-releasing element 44, which here consists of a large number of cooling fins 46. During operation, the heat pipes 40 and 42 absorb the heat which is generated by the xenon short arc lamp 18 and conveyed to the heat sink 36 and carry it to the heat-releasing element 44, i.e. to the outside of the housing 12. This is an entirely passive process, requiring no active current of air into or out of the housing 12. The surface area of the cooling fins 46 is large enough for the heat carried away by the heat pipes 40, 42 to be released into the environment without active cooling.

The power supply 16 also comprises a cooling plate 48 which dissipates the heat generated by the power supply 16. Soldered onto this cooling plate 48 is a heat pipe 49, which carries away the heat absorbed by the cooling plate 48. The heat pipe 49 is also connected to the heat-releasing element 44 such that the heat generated by the power supply 16 can likewise be carried away from the housing 12 without active cooling.

Figure 2:
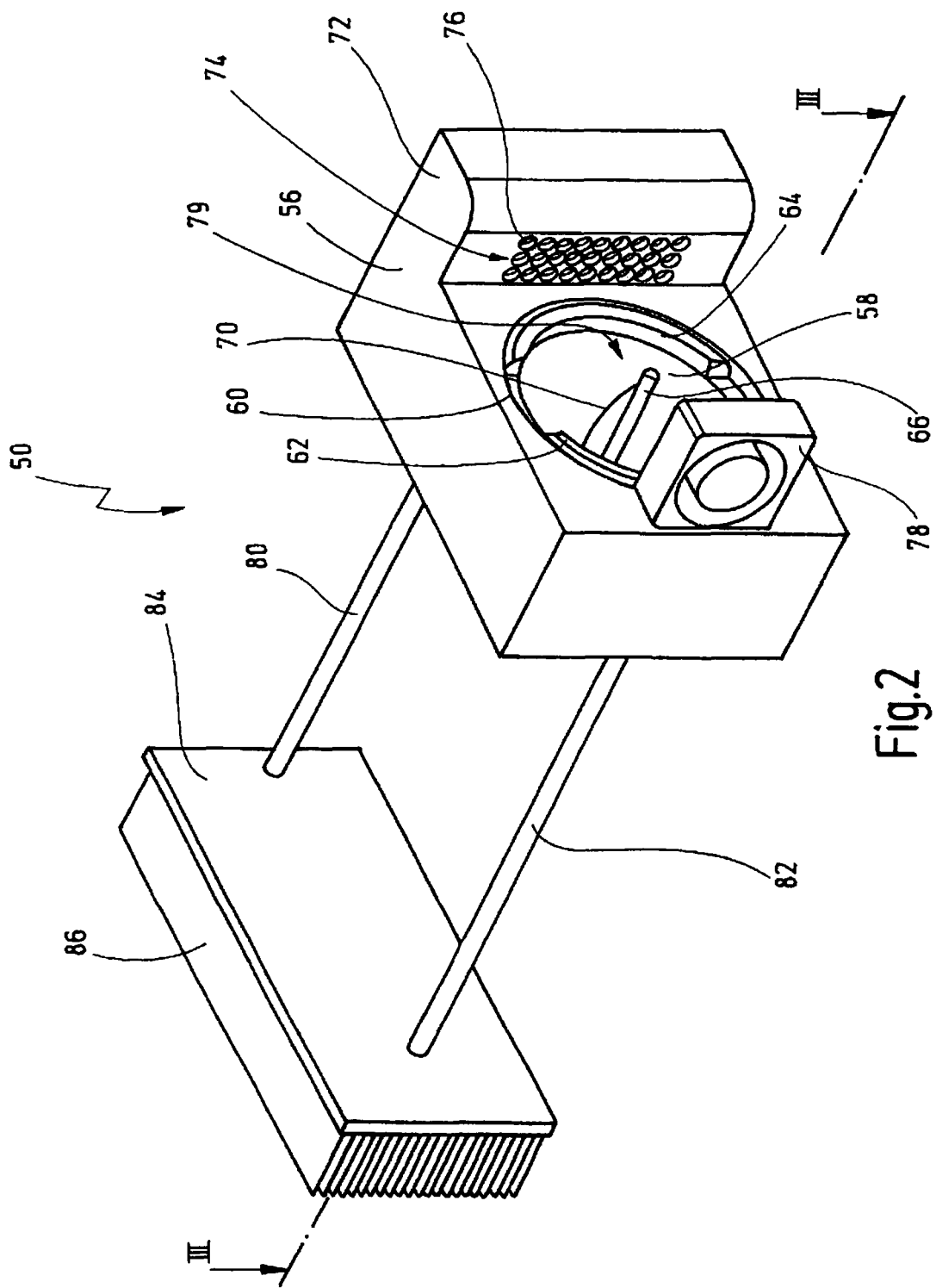
FIG. 2 shows an oblique view of a lamp module for a light source.

FIG. 2 shows a lamp module for a light source for endoscopy or microscopy, the lamp module as a whole being designated by the reference number 50.

The lamp module 50 comprises a heat sink 56, in which there is a xenon short arc lamp 58. This xenon short arc lamp is held in the heat sink 56 by means of clips 60 and 62. Also visible in this diagram is an electrode 66, which forms one of the two electrodes of the xenon short arc lamp 58, and a lead 70, by which the electrode 66 can be supplied with power.

The heat sink 56 also comprises a flank 72, which projects beyond the xenon short arc lamp 58. In this flank 72 there are structures that air can pass through 74, in the form of bored holes 76.

On the side of the heat sink 56 that is opposite to the flank 72 there is also a fan 78 which can generate a current of air across a radiating surface 79 of the xenon short arc lamp 58 in the direction of the flank 72.

Emerging from the back of the heat sink there are two heat pipes 80 and 82 which connect the heat sink to a heat-releasing element 84, which, in turn, comprises a large number of cooling fins 86.

Figure 3:
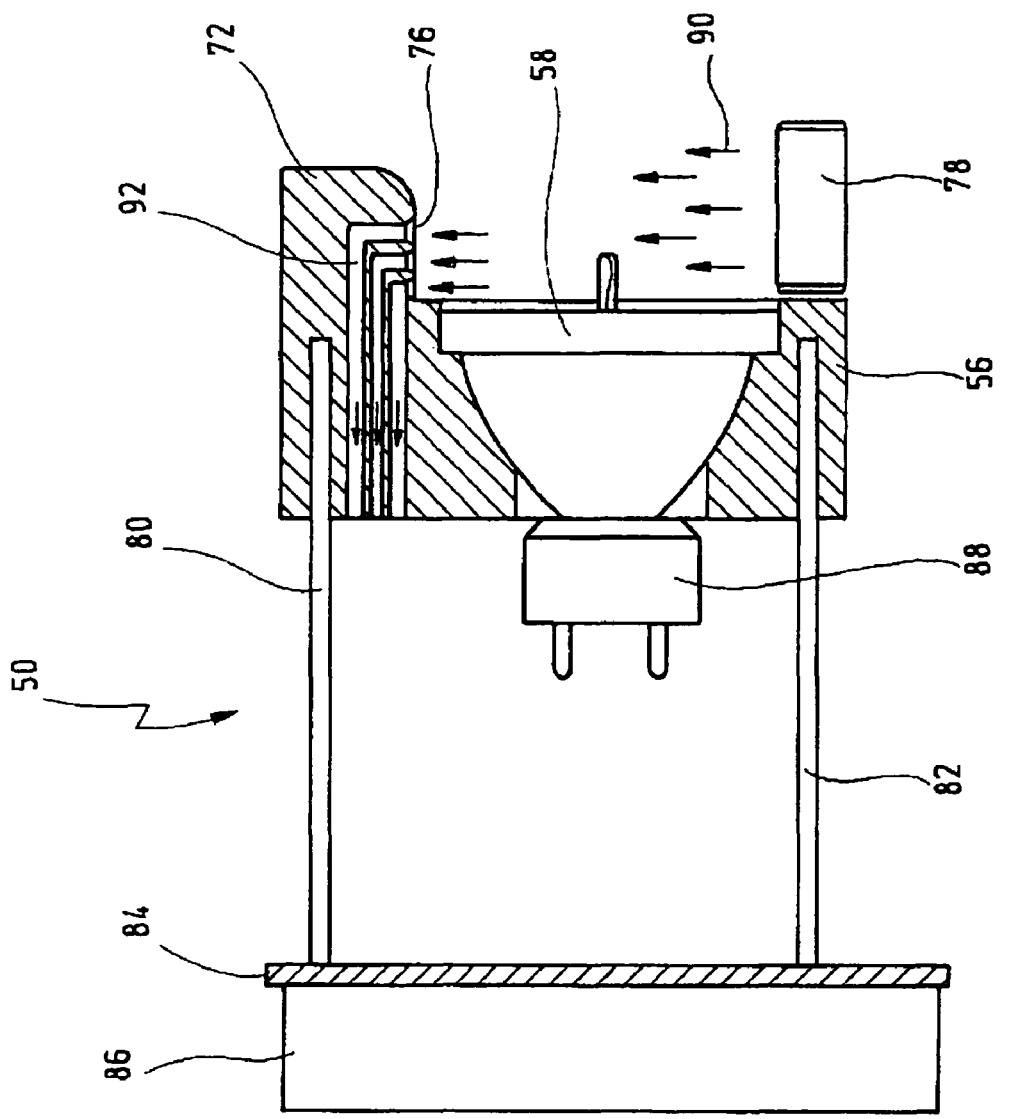
FIG. 3 shows a partial section through the lamp module shown in FIG. 2, along the line III-III.

FIG. 3 shows that these heat pipes 80 and 82 in turn run into holes bored in the heat sink 56.

FIG. 3 also shows that on the back of the xenon short arc lamp 58 there is a plug 88, by which the lamp can be supplied with power.

During operation, the heat given off at the sides of the xenon short arc lamp 58 passes to the heat sink 56 and is carried by the latter to the heat pipes 80 and 82. These heat pipes 80 and 82 draw the heat away in the direction of the heat-releasing element 84, the heat-releasing element 84 releasing the absorbed heat into the environment via the cooling fins 86.

The fan 78 can generate a current of air in the direction of the arrows 90. This current of air passes along the radiating surface 79 of the xenon short arc lamp 58 in the direction of the flank 72. As it does so, the current of air absorbs the heat which the xenon short arc lamp 58 emits at its radiating surface 79, and heats up. The heated current of air enters the bored holes 76, which continue, in the form of conduits 92, in the heat sink 56. Whilst flowing through the heat sink 56 the current of air releases some of the absorbed heat to the heat sink 56; the heat sink 56 can then carry this heat away via the heat pipes 80 and 82. Furthermore, the conduits 92 run alongside the heat pipe 80 for a certain distance, thereby greatly improving the dissipation of heat from the heated current of air into the heat pipe 80, such that the current of air emerging from the back of the heat sink 56 is already much cooler.

A build up of heat at the radiating surface 79 of the xenon short arc lamp 58 is thus effectively avoided.

Although a fan is used in this embodiment, the current of air generated by this fan flows entirely within the housing, with the result that no contamination of a sterile environment can occur.

Figure 4:
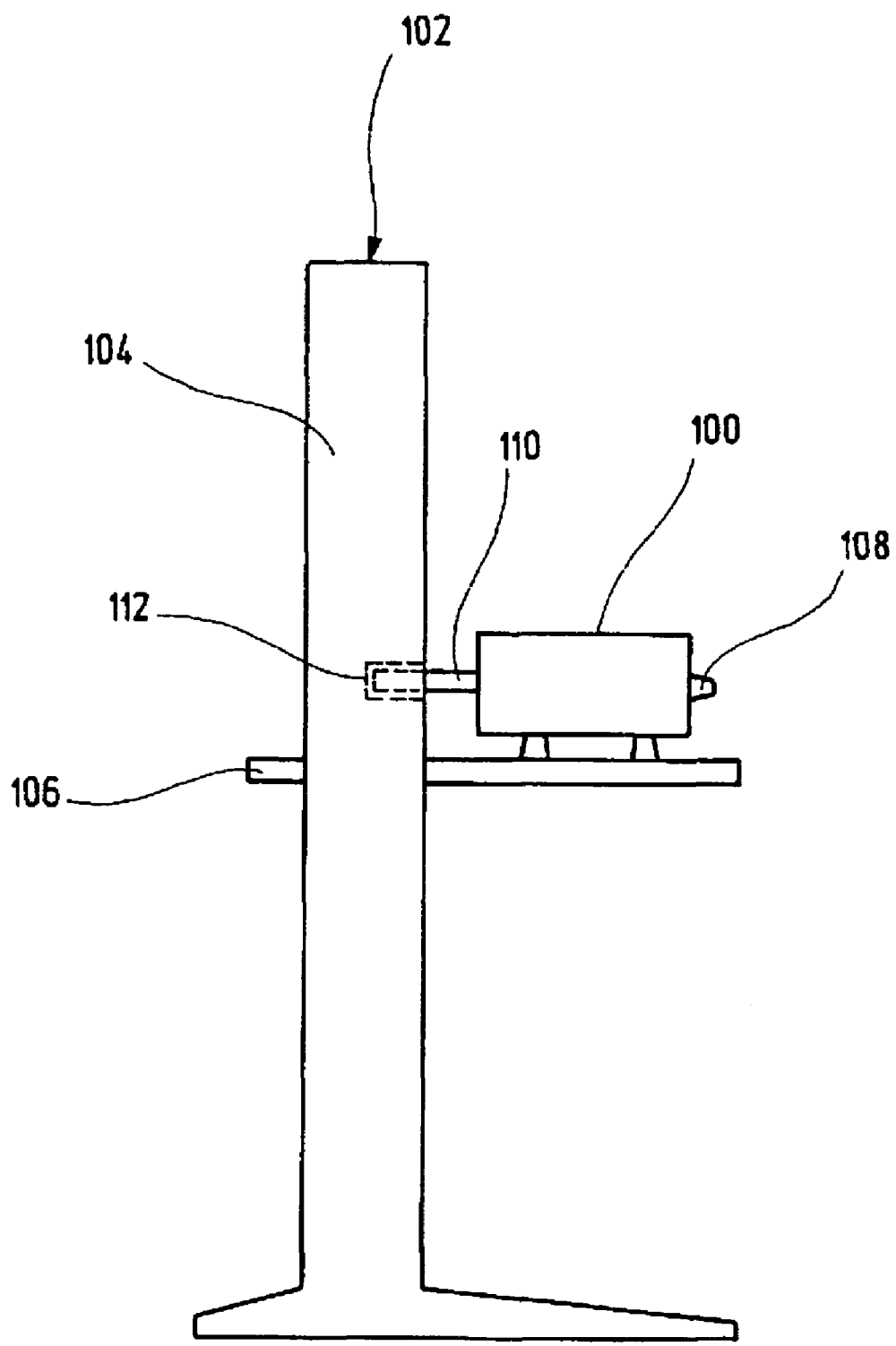
FIG. 4 shows a light source mounted on a support.

FIG. 4 shows a light source which as a whole is designated by the reference number 100.

The light source 100 is mounted on a support 102, which is here designed in the form of a rack. This support 102 comprises two side parts, which are parallel to each other, with only side part 104 being visible here. Between these side parts is a plate 106, on which sits the light source 100.

On the front of the light source 100 there is a connector 108 which can be used to connect a light guide. By means of this connector 108, light from the light source 100 can be fed into e.g. the light guide of an endoscope and be used to illuminate an area to be viewed with an endoscope.

At the back of the light source 100 their is the back end of a heat pipe 110, which is here not visible, connected, at its front, to a heat sink of a lamp module of the light source 100 and which carries heat away from this lamp module to the outside of the light source 100.

This heat pipe 110 is partially inserted in a hole 112 bored into the side part 104, as shown here by broken lines.

Between the heat pipe 110 and the hole 112 bored into the side part 104 there is also a thermally conductive paste which facilitates the transfer of heat from the heat pipe 110 to the side part 104.

In this embodiment, the heat carried away from the light source 100 by the heat pipe 110 is transferred to the side part 104. In this case a separate heat-dissipating element is no longer needed, as the side part 104 serves as a heat-dissipating element. Because the heat pipe 110 is only inserted into the side part 104, other devices that may likewise be equipped with heat pipes can also be used with the support 102 in a modular fashion. The side part 104 may also accommodate the heat pipes of several instruments and act as a "heat sink bus".

What is claimed is:

1. A light source for endoscopy or microscopy, comprising:
a lamp having a back side, a left side, and a right side;
a holder being in contact with at least said back side;
a heat sink;
said left side, and said right side are placed at least partially within said heat sink and are each in contact with said heat sink;
said holder being placed within said heat sink and being in contact with said heat sink;
at least one heat pipe connected to said heat sink for dissipating heat from said lamp and transferred to said heat sink;
at least one of a heat-accumulating and a heat-releasing element, whereby said at least one heat pipe is thermally connected to said at least one of a heat-accumulating and a heat-releasing element at a site some way removed from said heat sink, and whereby said at least one of a heat-accumulating and a heat-releasing element comprises microstructuring; and an electrically highly insulating layer between said lamp and said heat sink and said holder.

2. The light source according to claim 1, wherein said electrically highly insulating layer is thermally conductive.

3. The light source according to claim 1, wherein said electrically highly insulating layer is designed so as to reduce structure-borne sound.

4. The light source according to claim 1, wherein said electrically highly insulating layer consists of a nitride ceramic.

5. The light source according to claim 4, wherein said electrically highly insulating layer consists of aluminium nitride ceramic.

6. The light source according to claim 1, wherein said electrically highly insulating layer comprises a layer of copper on at least one surface.

7. The light source according to claim 6, wherein said electrically highly insulating layer comprises a layer of copper on all surfaces.

8. The light source according to claim 1, wherein said at least one of a heat-accumulating and a heat-releasing element can be thermally connected to several heat pipes.

9. The light source according to claim 8, wherein said several heat pipes belong to different devices.

10. The light source according to claim 1, further comprising a support for the light source, wherein said at least one heat pipe can be thermally connected to said support for said light source.

11. The light source according to claim 1, further comprising at least one fan, which generates a current of air across said radiating surface of said lamp.

12. The light source according to claim 11, wherein said heat sink comprises a flank, which projects beyond said radiating surface of said lamp and which is sited downstream of said radiating surface of said lamp in said current of air that can be generated by said fan.

13. The light source according to claim 12, wherein said flank comprises structures that air can pass through.

14. The light source according to claim 13, wherein said structures that air can pass through run at least part way along said at least one heat pipe.

15. The light source according to claim 1, further comprising a power supply to supply said lamp with power, said power supply comprising at least one heat pipe to dissipate said heat that is generated.

* * * * *